(12) United States Patent
Bechmann et al.

(10) Patent No.: US 7,736,589 B2
(45) Date of Patent: Jun. 15, 2010

(54) AUTOMATED MECHANICAL STRESS ASSAY FOR SCREENING CLEANING INGREDIENTS

(75) Inventors: Georg Rudolf Theobald Bechmann, Wezembeek-Oppem (BE); Steven Paul Georges Cooremans, Buggenhout (BE); Michael Godskesen, Vedbaek (DK); Soren Kjaerulff, Vanlose (DK)

(73) Assignee: Novozymes A/S, Bagsvaerd (DK)

( * ) Notice: Subject to any disclaimer, the term of this patent is extended or adjusted under 35 U.S.C. 154(b) by 461 days.

(21) Appl. No.: 11/474,593

(22) Filed: Jun. 26, 2006

(65) Prior Publication Data

US 2006/0240557 A1    Oct. 26, 2006

Related U.S. Application Data

(62) Division of application No. 09/995,321, filed on Nov. 27, 2001, now abandoned.

(60) Provisional application No. 60/257,068, filed on Dec. 20, 2000.

(30) Foreign Application Priority Data

Nov. 27, 2000   (DK) ............................. 2000 01781

(51) Int. Cl.
  *G01N 33/00*   (2006.01)
(52) U.S. Cl. .................... 422/68.1; 422/50; 422/99; 422/102; 422/103
(58) Field of Classification Search ............ 422/50, 422/68.1, 99, 100, 102, 103
See application file for complete search history.

(56) References Cited

U.S. PATENT DOCUMENTS

| | | | |
|---|---|---|---|
| 3,094,373 | A | 6/1963 | Luechauer |
| 3,176,716 | A | 4/1965 | Bucknell et al. |
| 4,493,783 | A | 1/1985 | Su et al. |
| 4,529,880 | A | 7/1985 | Merrill et al. |
| 4,847,089 | A | 7/1989 | Kramer et al. |
| 5,044,128 | A | 9/1991 | Nakano |
| 5,346,303 | A | 9/1994 | Heinonen et al. |
| 5,858,770 | A | 1/1999 | Perlman |
| 6,233,771 | B1 * | 5/2001 | Hortel et al. ............ 8/150 |
| 2002/0081748 | A1 * | 6/2002 | Roberts et al. ......... 436/174 |

FOREIGN PATENT DOCUMENTS

| | | |
|---|---|---|
| EP | 301583 | 7/1988 |
| FR | 1437055 | 4/1966 |
| GB | 624054 | 5/1949 |
| WO | WO 99/34011 | 7/1999 |
| WO | WO 99/44742 | 9/1999 |

\* cited by examiner

*Primary Examiner*—Sam P Siefke
(74) *Attorney, Agent, or Firm*—Kristin J. McNamara

(57) ABSTRACT

A method for testing cleaning effect of a compound or compositions is disclosed. The method comprises:
(a) Preparing a liquid sample of less than 10 ml comprising the test compound,
(b) applying liquid sample to a stained surface,
(c) applying mechanical stress to the stained surface by contacting it with a body present in the liquid sample,
(d) evaluating the cleaning effect of applying solution and mechanical stress on the stained surface.

20 Claims, 11 Drawing Sheets

0  40  20  10  5  0     0  40  20  10  5  0
Nanomoles per liter 0  40  20  10  5  0    0  40  20  10  5  0
Nanomoles per liter

AUTOMATED MECHANICAL STRESS ASSAY FOR SCREENING CLEANING INGREDIENTS

CROSS-REFERENCE TO RELATED APPLICATIONS

This application is a divisional of application Ser. No. 09/995,321 filed on Nov. 27, 2001 now abandoned which claims priority under 35 U.S.C. 119, of Danish application no. PA 2000 01781, filed Nov. 27, 2000, and the benefit of U.S. provisional application No. 60/257,068 filed Dec. 20, 2000, the contents of which are fully incorporated herein by reference.

FIELD OF THE INVENTION

This invention relates to an automated assay for testing real application performance of cleaning ingredients by testing them on mechanically stressed surfaces. The invention also relates to surfaces and other devices adapted for application in the automated assay and to cleaning ingredient identified by the assay and subsequently produced.

BACKGROUND OF THE INVENTION

It has been the object for researchers in the detergent industry to continuously search for new ingredients for use in cleaning compositions, which improves the cleaning effects of these compositions. In the field of surface cleaning, such as textiles of fabrics most people believe, that the flow of a liquid cleaning solution also called the washing liquor against and/or through a surface is sufficient for achieving a good cleaning process and accordingly that such conditions are suitable when the cleaning effect of new cleaning ingredients and/or compositions are evaluated to identify improvements.

Various artificial methods has over time been developed to provide tools for simulating a cleaning process and for testing cleaning effects. However using artificial methods often results in the finding of promising cleaning ingredients or compositions, which despite the predictions from the artificial methods does not provide the expected improvement when applied to real cleaning processes. Accordingly, in order to test and make reliable predictions on the cleaning effect of new ingredients or compositions, the skilled person has had adopt full scale cleaning processes and real surfaces, such as cleaning fabrics in a washing machine to provide useful results.

WO 99/34011 describes a method for assaying wash performance of new enzymes and/or detergent formulations.

The published Danish patent application PA 1997 00507 describes an assay for analyzing cellulolytic detergent enzymes.

SUMMARY OF THE INVENTION

Our research has shown that, besides contact between washing liquor and a fabric, the mechanical stress, which in real life applications is conferred to the fabric, is also of major importance. However, tests using full scale washing methods are difficult to automate and has a very limited sampling capacity rendering these method expensive and laborious. Moreover, some effects in a cleaning process may be very difficult or even impossible to assess using full scale washing methods. The present invention enables us of remedying these limitations by providing:

A method for testing cleaning effect of a compound or compositions thereof said method comprising:
(a) Preparing a liquid sample of less than 10 ml comprising the test compound,
(b) applying liquid sample to a stained surface,
(c) applying mechanical stress to the stained surface by contacting it with a body present in the liquid sample,
(d) evaluating the cleaning effect of applying solution and mechanical stress on the stained surface.

As this method is particularly suitable for automated testing of small volume samples, the invention also relates to a device developed for testing cleaning effect of a composition, said device comprising:
(a) at least one container having a volume of less than 10 ml, preferably less than 2 ml, most preferably less than 0.2 ml,
(b) at least one body capable of moving inside the container,
(c) at least one stained surface and
(d) means for providing movement of the body relatively to the stained surface.

The invention in accordance with these aspects provides means easily automated for testing of cleaning compositions, means which, through the use of small test samples less than 10 ml, preferably less than 2 ml, most preferably less than 0.2 ml, offers a large sampling capacity and through the element of mechanical stress offers simulation of the cleaning process comparable to real life or full scale cleaning processes.

BRIEF DESCRIPTION OF THE TABLES AND DRAWING

DETAILED DESCRIPTION OF THE INVENTION

The Method

Figure 1:
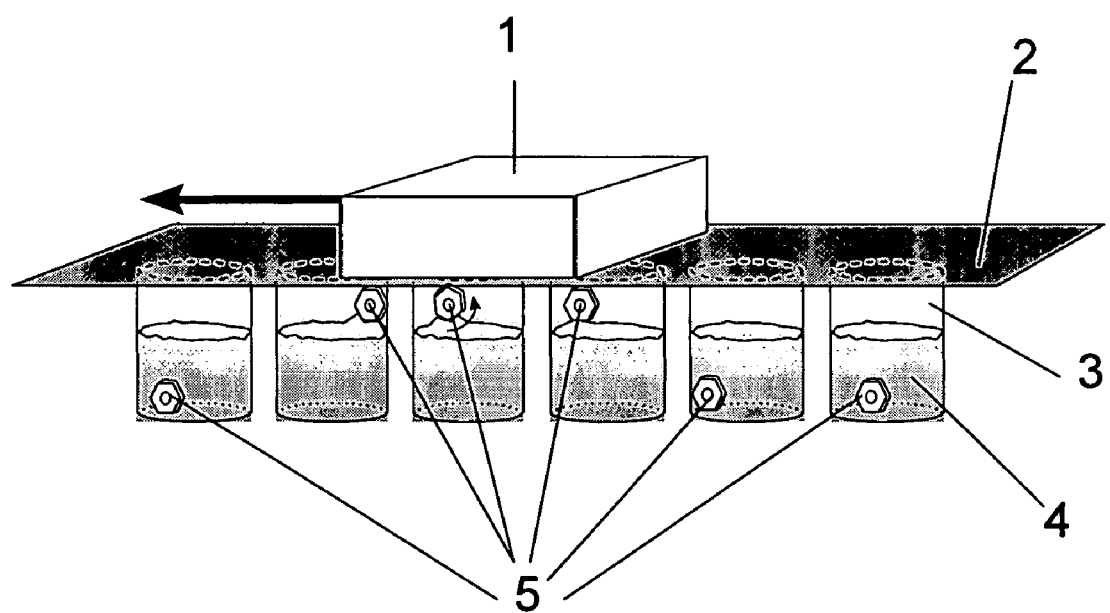
FIG. 1 is a drawing showing the principle of using a permanent magnet for providing mechanical force to a stained fabric.

One object of the invention is to provide a method for testing the cleaning effect of compounds on a stained surface using only small sample volumes less than 10 ml while, but which simulates and is comparable to real cleaning processes performed e.g. in a washing machine. One challenge in developing such a method is the implementation of the mechanical stress factor in a small sample volume system. It is to be understood that the system is a collection of functional members or tools used to carry out the method of the invention such as containers, stained surfaces, bodies or samples, and/or means for sealing, temperature control, pressure control etc. as described, infra.

The method we have developed, simulating full scale cleaning of surfaces, is easily automated and it is possible and even feasible to employ conventional testing vessels e.g. arrays of small containers, such as wells of a micro plate. The method and devices developed for performing the method allows to simulate cleaning processes on surfaces like fabrics at a micro scale even using extremely small sample volumes such as below 50 μl. The evaluation of cleaning effect of compounds such as new enzymes, can be done using this method at a 50.000 to 500.000 times smaller quantities than it is required for a full scale cleaning process. Basically the method provides a predictive system with the capability to be incorporated in high throughput facilities as it is established in the pharmaceutical industry. This new tool can therefore accelerate dramatically the development effort of new and improved cleaning compounds and/or compositions by providing the capability to test ingredients at high numbers and of low quantities.

The Test Compound

The purpose of the present invention is to provide means of identifying compounds or compositions thereof providing improved cleaning of a stained surface.

The compound or compositions thereof in the context of the invention is preferably selected from compounds known to be incorporated in detergent compositions such as enzymes and/or enzyme stabilizers, inhibitors, enhancers, co-factors, builders, builder systems, bleach systems, bleach activators, metal-containing bleach catalyst, optical brighteners, non-ionic-, anionic-, cationic-, zwitterionic and amphoteric surfactants, fabric softening agents, softening clays, clay flocculants, dye-transfer inhibiting agents, polymeric soil release agents, clay soil removal agents, anti-soil redeposition agents, polymeric dispersing systems, chelating agents, alkoxylated polycarboxylates, perfumes, perfume systems, carrier systems, dyes and pigments, fabric care agents, color care agents and the like. Further, also compounds which are present in the water used to form a washing liquor may contain relevant test compounds. Such compounds include dissolved salts, such as salts of Ca and/or Mg which will determine the hardness of the water, or salts of carbonate, nitrate, chloride, sulfate and/or phosphate.

Typical enzymes used in fabric care and cleaning products are proteases, lipases, amylases, cellulose hydrolyzing enzymes such as cellulases, carbohydrases such as mannanases or pectatlyases, transferases, oxidoreductases and like, preferably the enzymes are alkaline enzymes characterized by having their catalytic optimums between pH 7-12, more preferably high alkaline having their catalytic optimums between pH 9-12.

The Liquid Sample

In the present invention a liquid sample is prepared comprising the compound and/or the composition to be tested. The sample is preferably an aqueous solution or dispersion of the test compound or composition, but it may also be non-aqueous of nature, which may be relevant when testing compounds suitable for use in non-aqueous cleaning liquids.

In a preferred embodiment the liquid sample is prepared by first preparing a base solution and/or dispersion and transferring predefined amounts hereof to a test vessel or container. The compound or composition may then be added to the vessels in minute amounts, preferably in solution. In accordance with the invention, the liquid sample thus prepared have a volume of less than 10 ml, preferably less than 2 ml, most preferably less than 0.2 ml, but the method works with considerably less volume, which is feasible to increase the sample capacity. Accordingly the sample volume is comparable to the well volume of commercially available micro plates. A suitable volume is less than the well volume of a 24 well micro plate, preferably less than the volume of a well on a 96, 384 or 1536 well plate. Based on the type of micro plate, the volume can be chosen between 5-95% of the volume of the well, which is 3.7 ml, 320 μl, 160 μl, and 14 μl, respectively.

The Surface

Surface materials relevant to be employed in the present invention are materials used in real life, which are subjected to cleaning processes. Such materials may be inorganic such as metal, ceramic, glass, enamel concrete, rock, marble, gypsum or composite combinations thereof. The material may also be mainly organic by nature such as plastic, rubber, wood, paper, leather, fur, paint or fabric. A preferred surface is a fabric. The fabric may be any fabric made from natural plant fibers, animal based fibres or synthetic fibres or combinations thereof. The fabric may be woven or non-woven or soft or stiff. Most preferred fabrics are cellulose containing fabrics such textiles (woven) and tissues (non woven) and animal based fabrics such as wool.

A stained surface may be achieved by employing any conventional staining techniques associating a stain comprising a traceable compound or composition to the surface and/or associating the traceable compound or composition itself to the surface.

Suitable traceable compounds includes dyes such as light absorbing or fluorescent dye, radioactive compounds, reactive compounds, such a catalysts and/or activators capable of performing measurable interaction with substrates. Such compound may be associated directly or indirectly to the surface by covalent bonding, ionic bonding and/or hydrogen bonding.

The surface may also be stained with a particulate composition such carbon particles, e.g. carbon black or iron oxides.

In a preferred embodiment the surface is stained by a soiling composition comprising the traceable compound or composition. Such soiling composition is preferably a naturally occurring soiling such as grass, mud, clay, coffee, tea, blood, egg, lard, moulds (damp stained) or the composition may made of processed naturally occurring soiling, such as butter, processed meat, dyed lard, oil, make up, spice blends, processed tomatoes (ketchup or puree), chocolate, ice cream, cacao, baby food and the like. The soiling may also preferably be a man made composition comprising compounds selected from refined protein compositions, refined polysaccharide compositions, refined fatty acid compositions, refined triglyceride compositions or other refined biological or non-biological compounds.

Most fabrics are stained by applying the staining material as it is or as an aqueous solution onto the fabric surface by soaking, brushing and/or spraying. The stained fabrics will be dried before testing. There is also a group of colourless materials, which bind soil and particles onto surfaces. Carbohydrates like Guaran Gum, Locust Bean Gum and starch and the like are belonging to this group of materials, which are attracting soil materials. One example of preparing stain with such materials is as follows:

1) Dissolving the soil binding material Guar Gum in a aqueous solution at a level of 0.1 to 1%.
2) Applying the solution onto the fabric surface by soaking, brushing, or spraying onto the surface.
3) Removal of the access gum material by washing the coated fabrics in a commercial washing machine (Miele, short cycle, 40° C.) without detergent.
4) Staining of the coated fabrics in a commercial washing machine (Miele, short cycle, 40° C.) by adding 0.1 to 1% of clay, carbon black, iron oxide and/or other pigments/particular soiling materials into the wash machine without detergent.

Fabric surfaces having a range of different stainings are commercially available under the trade name EMPA® swatches marketed by EMPA St. Gallen, Lerchfeldstrasse 5, CH-9014 St. Gallen, Switzerland.

The Body

For applying mechanical stress to the surface the present invention requires a body present in the liquid sample comprising the test compound. It is necessary that the body has a size and shape which allows the body to go into the container holding the liquid sample, so that the body is present in the liquid sample. Preferably the body has a size and a shape, which allows the body to move in multiple directions within the container holding the sample and the body. The size and shape of the body should also preferably allow the body to be submersed in the sample.

The body is made of a material, which is preferably insoluble in the solution. The body is preferably rigid, but it may also be flexible and it may have a smooth or a rough surface. It is important that the body material is predominately inert, i.e. that the body does not chemically interact with the sample or vice versa. Accordingly the body material is made from durable materials. Such materials may be inorganic such as metal, ceramic, glass, enamel concrete, rock, marble, gypsum or composite combinations thereof or organic such as plastic, rubber or combinations thereof. Preferably the material is sufficiently ductile to prevent breakage of the body upon collision with the stained surface or container walls. The body may also be any suitable material coated with said inert and ductile material.

In a preferred embodiment the body comprises a metal, more preferably a ferromagnetic metal such as iron or alloys thereof or a composite comprising such metals or alloys. To inhibit corrosion of metals, the body is preferably coated with a layer of inert material such as organic polymers, separating the metal(s) from any outer corrosive media.

In this case the body may be any suitable nut, bolt, screw, bed or ball, preferred bodies have a surface comprising at least one edge or corner like a rectangular body.

Any shape like spherical, round-flat, disk shape, cube shape, elongated cube shape, cylindrical round shape, cylindrical rectangular shape, star shape, hexagonal shape, and like is suitable which fulfils the requirements for size and shape to fit into the test container.

The choice of body material is important for the choice of method for transferring kinetic energy (movement) to the body. The size, shape, mass and surface texture is important for the type and amount of mechanical stress the body is capable of conferring to the stained surface. Depending on the type of compound to be tested excellent results have been obtained with 3-5 rectangular stainless steel bodies (3×1.6× 1.9 mm) per container in a 96 well plate or stainless steel balls or beads having a diameter of 3 mm or less.

Application of Liquid Sample and Mechanical Stress to the Stained Surface.

In the method of the invention the stained surface must be placed where the body and the sample solution has access to the stained surface. Having the sample and the body in a container the stained surface may be placed in any position from the bottom to the top of the container. Preferably the stained surface is placed at the top or the bottom of the container and more preferably the stained surface functions as a cover on an opening in the container.

When the stained surface is placed below sample level in the container (submersed), the application of the liquid sample to the stained surface is continuous, while when the stained surface is placed above sample level in the container application of the liquid sample to the surface depends on movement of liquid sample relative to the stained surface to allow liquid to contact the surface. This may be achieved by movement of the liquid, movement of the stained surface a combination thereof.

The mechanical stress may be conferred to the stained surface by providing movement of the body relative to the stained surface, which allows the body to collide with the stained surface. This may be achieved by movement of the body, movement of the stained surface a combination thereof.

In the preferred embodiment of the stained surface acting as a lid on top of the container, the application of sample liquid and mechanical stress to the stained surface may advantageously be combined. In this case the mechanical stress may be provided to the to the stained surface by moving the body and allowing it to collide with the surface. However, as the body moves from having contact with the liquid sample, e.g. by being submersed therein, some sample liquid will adhere to the body and when the body collide with the stained surface some of liquid sample adhering to the body will be deposited or applied on the surface. Further, repeating movement and collision between surface and body will provide exchange of previously deposited sample and fresh sample, so that changes in the sample liquid deposited on the stained surface, e.g. as a result of interaction between stain and sample liquid, will be equilibrating with un-deposited sample liquid. Accordingly, by employing this system application of both liquid sample and mechanical stress may be achieved by moving the body. This system further solves problems related to having the stained surface present inside the container, e.g. submersed in the liquid sample. Firstly, such submersed surfaces has to be cut into very small pieces to fit into the containers encompassed by the invention, which may be a tedious procedure, secondly, a submersed surface may interfere with movement of the body, as stained surface and body may get entangled with each other inhibiting or changing the movement pattern, third, the mechanical stress conferred to the stained surface by collision with the body may occur in an irregular and non-reproducible manner, introducing increased levels of noise into the evaluation of the cleaning effect, fourth, if evaluation of the cleaning effect is includes analyzing the stained surface this process is difficult to automate because each stained surface is to handled individually. The second, third and fourth problem may, however, be somewhat remedied by attaching the stained surface to the bottom of the container, which may be feasible if the method for evaluating the cleaning effect of the liquid samples allows such a setup, e.g. if measurement can be made on the liquid sample or on the stained surface through the bottom wall of the container.

Movement of liquid sample, the body and/or the stained surface may be provided for by employing a force, preferably an oscillating force. The term oscillating as used in this context means that the force is following a directional and amplitudical repetition scheme, preferably a periodical pattern, in amplitude and direction. As an example an applied force may repeatedly act first upwards and then downwards on the body (or any other element of the invention) and/or it may act first towards one side and the towards the opposite side and/or from front to back. The force might be applied in a regular, periodic oscillating manner or completely in random, non-periodic irregular manner. An oscillating force also encompasses combinations of these directional forces, i.e. in altering force patterns such as applying upward and downwards force for defined period of time followed by applying side wards forces for period of time followed again by up and downwards forces and so on. By applying an oscillating force the collisions between body and stained surface are repeated many times conferring significant mechanical stress to the stained surface.

Various types of forces may be employed to achieve movement of the liquid sample, the body and/or the stained surface.

The oscillating force may be mechanical of nature e.g. by applying external movement to all or selected parts of the system, which subsequently confers movement to the liquid sample, the body and/or the stained surface. This may be achieved by subjecting the system or parts of the system to shaking and/or vibration, e.g. by vibrating the container holding the liquid sample, the body and the stained surface. Mechanical forces includes subjecting the system or parts of the system to motion waves such as sound waves, preferably of higher frequency such as ultra sonic waves.

Other suitable forces are forces capable of acting on selected system elements having special properties. Such forces include magnetic, electromagnetic, electrostatic and/or electrical forces. Magnetic or electromagnetic forces for example act only on magnetizable materials such as ferromagnetic materials. Accordingly it is possible to employ forces, which acts only on selected elements of the system. One advantage of applying these types of forces is that these forces act on susceptible elements though force fields, which may act on susceptible materials over distance penetrating non-susceptible materials. Accordingly it is possible the apply force to a system element, such as the susceptible body, e.g. through a non-susceptible container wall. As an example a magnetic force field will act on an ferromagnetic containing body through the wall of a plastic, glass or non-ferromagnetic metal container.

In a preferred embodiment the force includes at least one force field selected from magnetic field, electromagnetic field, electrostatic field and electric field.

In a further preferred embodiment is preferred to employ a force acting on and moving the body only whereby, as described supra, both application of liquid sample and mechanical stress to the stained surface may be achieved independent of the position of the surface. More preferably the force includes a magnetic or electromagnetic field and the body comprises a magnetically susceptible material, such as a ferromagnetic material. It is to be understood that in this embodiment, the force may also act on components of the liquid sample on a molecular level, such as ions or it may act on fixed members of the system elements, but it does not directly induce movement of the liquid sample, the stained surface, the container or other elements (such as tables, container holder etc.) used to carry out the method of the invention.

The present invention also encompasses employment of combinations of different force types such as combination of mechanical force and magnetic force fields.

In a most preferred embodiment the force is applied to a magnetizable body by moving a magnet relatively to the container containing the body, thus altering the magnetic field affecting the body or the force is a mechanical vibration force applied to an assembly comprising body, container and stained fabric.

A suitable system consists of a micro plate and a source of field force on top of the plate. A modification is an additional force field at the bottom of micro plate.

Evaluation of Cleaning Effect

Evaluation of the cleaning effect of a sample liquid may be achieved by analyzing the stained surface, the liquid sample or both after subjecting the stained surface to the liquid sample and the mechanical stress. A suitable choice of method will depend on the type of stain, which is used.

It may be feasible to measure changes of either surface or the liquid sample or both. Various methods are known to the art and includes optical methods, optical methods combined with coupled reaction between staining compounds and indicators, enzyme assays, physical measurements of altered surface properties chromatographic or fluorimetric methods, spectroscopic methods, radioactive labeling methods, immunochemical methods such as ELISA and more. If the stain is a more or less complex soiling composition it is usually more feasible to analyse the stained surface e.g. by measuring the stained surface reflectance of light with suitable reflectometers or calorimeters.

The Testing Device

As described, supra, this invention also relates to a device suitable for testing cleaning effect of a composition, said device comprising:
(a) at least one container having a volume of less than 10 ml, preferably less than 2 ml, most preferably less than 0.2 ml,
(b) at least one body capable of moving inside the container,
(c) at least one stained surface, preferably a stained fabric and
(d) means for providing movement of the body relatively to the stained surface.

The advantageous features of speed and capacity in testing compounds provided by the present invention relies to a major extent on the assembly of equipment making up the testing device. Accordingly, an important aspect of the invention is the practical applicability of the stained surface. In order to achieve the optimal capacity and speed in the present assay it is, as described supra, preferred to use a stained surface which functions as a lid on the container in which the test sample is placed. Within this embodiment it is further preferred that the stained surface, as a coherent entity, has a dimension, which makes it capable of acting as a lid on two or more containers simultaneously. More preferably the stained surface have a dimension, which makes it capable of acting as a lid on an array or arrays of containers simultaneously enables. The embodiment of using a stained surface having a dimension, which makes it capable of acting as a lid on numerous test containers is very important indeed not only considering test capacity but also considering the accuracy of the testing. For many stained surfaces, such as fabrics, there may be variations between different entities of the same type of surface. For example variations in the texture and firmness between different parts of a cloth, from which stained fabric sub-pieces are made, may cause variations between fabric sub-pieces in stainability and ability to interact with test compound(s). However, by choosing a test assembly which requires that the stained fabric has a certain dimension, which, as a coherent entity, is capable acting as a lid for numerous test containers, it is secured that the stained fabric used to test compounds in each individual container has a lowered variation in texture, firmness and staining, because it, taken as a coherent entity must originate from the same part or area of e.g. the cloth from which it is taken. The term "coherent" in this context is to be understood in the broadest sense, but preferably that the fabric is in one coherent woven or non woven piece without seams or stitches or other fastening means, which may make the fabric surface less uniform.

Accordingly, the present invention also relates to an assembly suitable for use in testing effect of cleaning ingredients, e.g. in the device as described above, which through a special combination of containers and stained fabric provide for high speed and capacity as well as good accuracy in testing cleaning ingredients, such as enzymes. Accordingly, the present invention provides an assembly comprising at least one container and a stained coherent fabric, wherein the container comprises at least one opening covered and/or lidded with the stained coherent fabric. The invention also encompasses an assembly comprising a container and a stained coherent fabric, wherein the container comprises two oppositely positioned openings and at least one, preferably both of said openings are covered and/or lidded with a stained coherent fabric. In one preferred embodiment the assembly further comprises least one body in each container for providing mechanical stress to the stained fabric, as described supra, preferably within the container. In another preferred embodiment the assembly comprises an array of containers, wherein each container comprises one or more openings and optionally one or more bodies and wherein the stained coherent fabric covers and/or lids at least one of the openings in each container. In a further preferred embodiment the array of containers is a micro plate comprising 24, 96, 384 or 1536 containers or wells and the stained coherent fabric have a preferred dimension within 0.2-10 cm by 0.2-15 cm, preferably a dimension enabling the stained fabric to cover all the wells in the micro plate.

The term "cover/lid" in this context is to be understood in the sense that the stained fabric covers the opening of a container by being in contact with the edges of the opening.

Preferably the assembly comprises an additional support lid or cover located in the assembly so that the fabric is placed between the support lid and the container opening. The support lid is preferably made from a material, which is impermeable to the liquid sample in the container and has a dimension which makes the support lid rigid enough to support the fabric and prevent the fabric from moving away from the opening when subjected to mechanical force. The assembly also preferably comprise means for fastening the support lid to the container so that the fabric may act as a sealing gasket.

Figure 3:
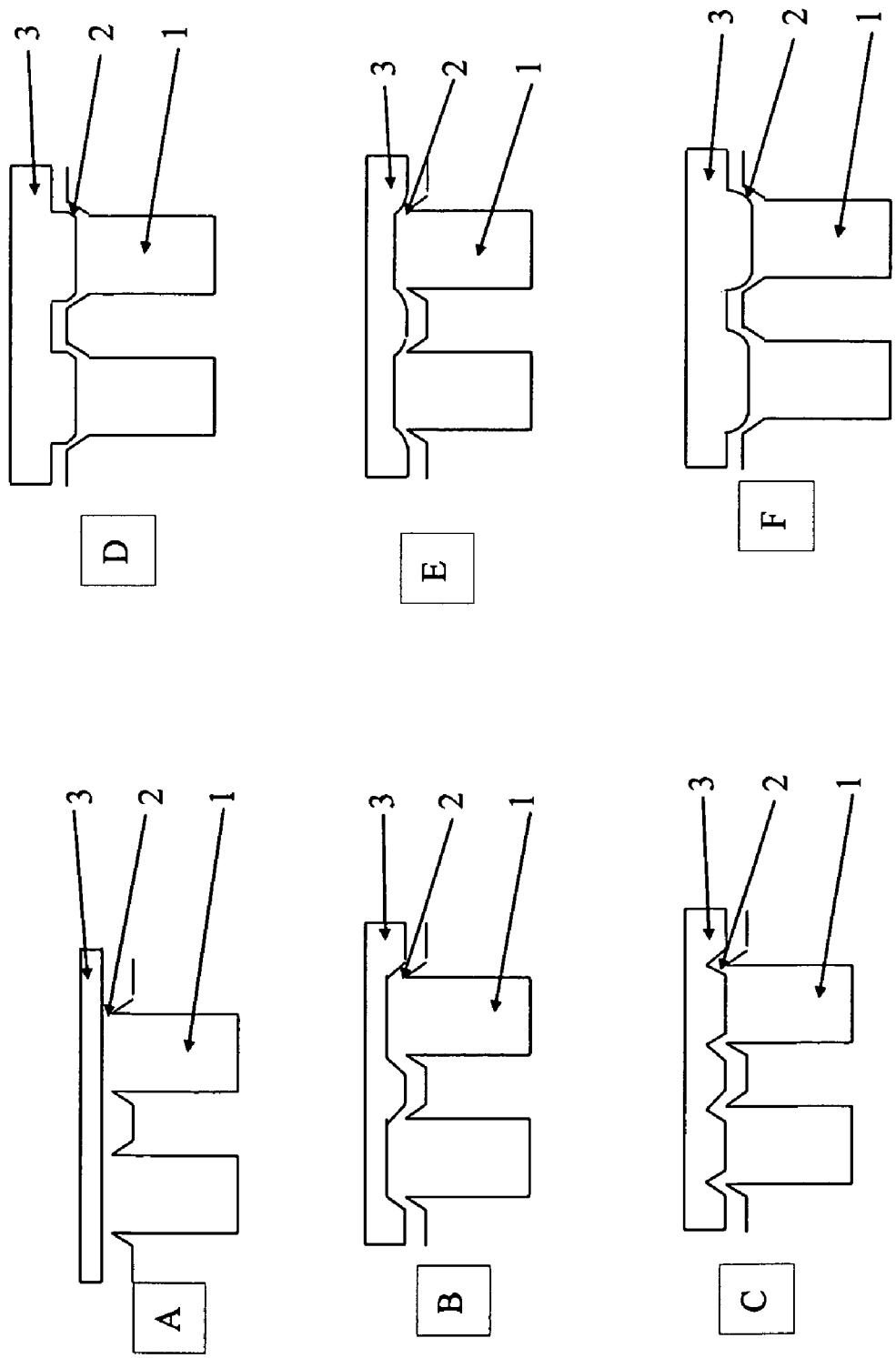
FIG. 3 is drawings showing cross sections of different types of assemblies suitable for use in testing effects of cleaning ingredients.

One important feature in this context is that the contact zone between the fabric and the edge of the opening is small so that the pressure holding the fabric in contact with the container opening, when the support lid is fastened to the container, is sufficient to seal the container, using the fabric as a gasket. This is important to prevent or inhibit that liquid sample from one container contaminates, through capillary movement, an adjacent container. To improve contact pressure between fabric and container opening by minimizing the contact zone, the edge of container openings and interconnecting surface between containers and the side of the support lid facing the fabric are designed so that they form a line toward each other instead of a surface. This can be achieved by designing the support lid and containers so that the interconnecting surface between containers in an array and the surface of the support lid facing the fabric are essentially unparallel, i.e. greater or less than about 180°. Examples of this design is given e.g. in FIG. 3.

Also other elements may be added to the assembly, such as devices for providing mechanical force to the body, the sample, the fabric or a combination, means for controlling temperature, devices for measuring properties of the stained fabric or the test sample. For convenience the assembly comprising container, stained fabric and optionally a support lid is from hereon referred to as the "primary assembly" and assemblies comprising additional elements are referred to as "secondary assemblies". Accordingly the present invention encompasses any test system comprising primary or secondary assemblies.

In one embodiment of the invention a secondary assembly comprises a device for providing mechanical force, the device preferably comprises a piston in a cylinder construction for generating vibration or shaking force, which is transferable to the stained fabric. Preferably the piston device is connected, via a rigid plate, suitable for mounting and/or fastening the primary assembly, to the primary assembly. The piston based device is preferably driven by a pneumatic or hydraulic system, using compression and/or expansion of air or liquid to move the piston relative to the cylinder. In a preferred embodiment the cylinder or the piston is fastened on the rigid plate at the opposite side (preferably to bottom side) of the primary assembly and this secondary assembly is connected to a stationary support construction via an elastic material capable of moderating movement of this secondary assembly. In this construction mechanical force in the form of vibration is transferred to the primary assembly (and to the stained fabric and movable body within the test container) by the weight displacement and/or acceleration by which ever of the cylinder or piston, which is not connected to the rigid plate. This displacement is achieved by moving the piston or cylinder relatively to the other elements of the secondary assembly by means of a hydraulic or pneumatic system. Such devices for providing mechanical force are commercially available e.g. from Copenhagen Vibrator Product, Denmark.

An alternative to the piston-cylinder construction is a device comprising an engine spinning a mass element, such as a driving wheel, having a heterogeneous mass distribution, said device connected to the primary device and to a stationary support construction via a rigid plate. To moderate movement the rigid plate may be connected to a stationary support via an elastic material, such as rubber. When the mass element spins, the heterogeneous mass distribution will cause repetitive displacement of mass and will confer vibration to the primary assembly and the container holding the test sample.

Figure 10:
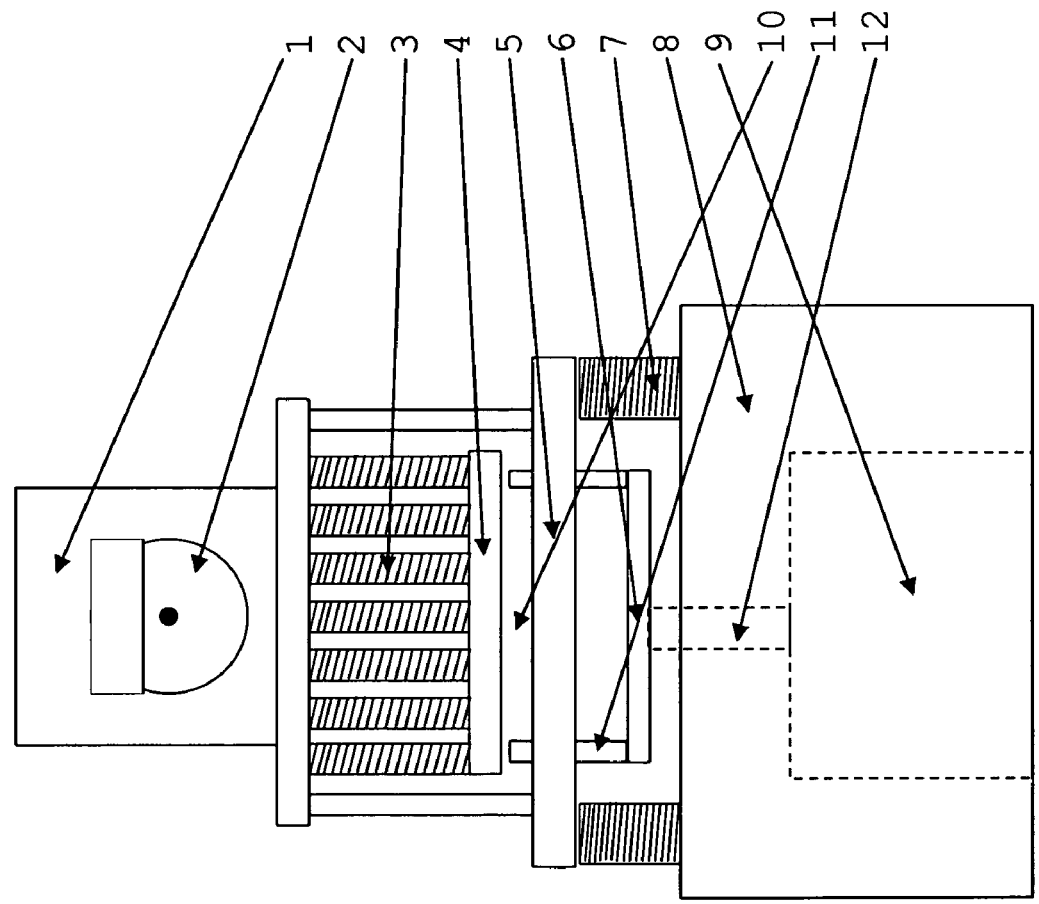
FIG. 10 shows a schematic cross sections of an assembled device particularly suitable for carrying out the method of the invention.

In a particular embodiment the secondary assembly comprise the element of the secondary assembly depicted in FIG. 10. Here at least one engine (1) (preferably two electric engines having opposite spin directions) is rigidly connected to a rigid plate (5) for holding a primary assembly. The engine(s) spins one or more heterogeneous mass elements (2) capable of vibrating the rigid holder plate (5). A rigid lid plate (4) is connected by flexible elements (3) (preferably one or more springs) to the engine(s) (1) and the rigid holder plate (5). Between the lid plate (4) and the holder plate (5) there is a slit (10) for holding a primary assembly. The width of the slit (10) is dimensioned so that the flexible elements has to be compressed in order to insert a primary assembly and so that the flexible elements (3) will press the lid plate (4) against the container openings of the primary assembly once inserted into the slit (10). The elements 1-5 are connected to a base construction (8) through flexible elements (7) (preferably one or more springs). The secondary assembly comprise means for compressing the flexible elements (3) holding the rigid lid plate (4) when the a primary assembly is to be inserted or removed. These compressing means may in particular be connected to base construction (8). The means for compressing the flexible elements (3) may comprise an engine driven gearbox (9) which e.g. via threaded bolt (12) and a rigid construction (6) may drive one or more rods (11), e.g. through holes or bushings in the holder plate (5) against the lid plate (4) whereby the flexible elements (3) are compressed. The engine(s) (1) may further be connected to means for controlling the rotation speed e.g. a frequency controller. Still further, the secondary assembly may comprise means for regulating the temperature of a primary assembly placed in the slit (10). In a particular embodiment the whole secondary assembly in encased in an insulated casing wherein the temperature is controlled by a thermostatted air heater. Hence the invention provides in this embodiment: An assembly comprising at least one engine capable of spinning at least one heterogeneously distributed mass, said engine rigidly connected to a rigid holder plate for holding an array of containers and said engine connected to a rigid lid plate via a first set of flexible elements and wherein the holder plate and the lid plate forms a slit for positioning an array of containers and wherein said holder plate is connected via a second set of flexible elements to a base construction, said second set of flexible elements allowing the vibrational movements of the holder plate, the lid plate, the engine and the first set of flexible elements.

In another embodiment the assembly comprises a magnetic device which comprises a permanent magnet or an electro-magnet. In the case of a permanent magnet such as a Neodymium Iron Boran magnet, the magnetic device also comprise means for providing movement of the magnet relative to a magnetizable body comprised in the container of the primary assembly applying an alternating magnetic force to a magnetizable body present in the container.

In a specific embodiment this secondary assembly preferably is a carousel construction comprising
(a) a horizontal rotatable support surface comprising means for fastening, in a position different from the rotational center, a container containing a movable and magnetizable body and a least one opening covered with the stained coherent fabric,
(b) a permanent magnet connected to the axis, enabling variation in the magnetic field applied to the container upon rotating the support and
(c) means for rotating either the magnet, the support surface or both so as to create a relative movement between magnet and support surface.

The magnet is preferably placed in a fixed position so that the support surface is the only movable part and so that the test container(s) upon rotation is allowed to come into sufficient proximity of the magnet so that a magnetic field is applied to the body in the test container, which is sufficient to move the body within the container towards the magnet.

The invention also relates to the use of a coherent stained fabric as cover and/or lid on an array of at least two, preferably at least 24, more preferably at least 96 containers having a volume of less than 10 ml for testing cleaning ingredients.

Special Method Embodiments

Although for most enzymes acting directly on the cellulose in textile, severe mechanical stress of the stained surface is important, we have also found that when testing cleaning effect of non cellulolytic enzymes such as protease, lipase amylase and oxidoreductase on stained fabric, the mechanical stress provided by repeatedly moving the sample liquid against the fabric surprisingly gives test results which is very similar to results obtained in real laundry processes. This may be achieved by shaking or vibrating containers holding the liquid samples and moving the liquid against the stained fabric. Combined with the finding that a coherent stained fabric may be used to test liquid samples in more than one container simultaneously by using the fabric as a lid and seal on the containers (see description of the primary assemblies, supra) these findings provide a powerful tool for automated testing of these enzymes. Accordingly, the present invention also relates to a method for testing cleaning effect of a non-cellulolytic enzymes said method comprising:
(a) Preparing liquid samples comprising the non-cellulolytic enzyme in an assembly according to any of the claims 30-40, with the proviso that the container does not contain a solid body capable of moving inside the container,
(b) repeatedly applying liquid sample to the stained fabric,
(c) evaluating the cleaning effect of applying solution on the stained fabric.

This embodiment of course also encompasses within step (a) use of all primary assemblies as described, supra for testing cleaning ingredients.

EXAMPLES

Example 1

Evaluation of Cleaning Effects of Mechanical Stress in a Model Washing Machine

Effect of Mechanical Stress on Stain Removal Performance:
Light reflectance values of fabrics having different stains washed in a Launder-O-Meter at low and at high mechanical conditions.

Preparation:
Stained fabrics were obtained from Equest Market Research Limited, Equest House, Greencroft Industrial Park, Annfield Plain, Stanley, Co. Durham, DH9 7YB, England, a Launder-O-Meter with 500 ml beakers was obtained from Roaches England LTD, Washtec and a liquid detergent Ariel Futur was used.

Test Procedure:
A wash solution of 200 ml city water with 1.3 ml Ariel Futur liquid detergent and 5 stained fabrics (4×4 cm) was added to each beaker. In beakers wherein low mechanical stress were to be tested no bodies were added, while in beakers wherein high mechanical stress were to be tested were added 10 Teflon coated star magnets (24 mm diameter) and 30 steel nuts (25 mm diameter). The stained fabric were washed in the Launder-O-meter for 30 minutes wash at 40° C. with or without.

Evaluation of Cleaning Effect:

Light reflectance values of the stained fabrics were measures by a Spectrafash 500 equipment from "datacolor international".

| L-values | burnt beef | make-up | grass/mud | chocolate ice-cream |
|---|---|---|---|---|
| original stain | 42.9 | 59.2 | 54.1 | 64.1 |
| washed with low mechanical stress | 57.4 | 63.5 | 72.8 | 74.1 |
| washed with high mechanical stress | 76.1 | 81.0 | 84.2 | 88.1 |
| clean fabric | 92.8 | 92.8 | 92.8 | 92.8 | noise level about +/− 1.5 units

From this experiment it can be observed that mechanical stress to the stained fabric has a significant effect on the cleaning effect of the detergent ingredients.

Example 2

Testing System 1

A test device was developed according to FIG. 1, wherein 1 is a movable permanent Neodymium Iron Boran magnet (20×2.5×1.3 cm) with 12200 Gauss strength; 2=a stained fabric; 3 are wells of a 96 well micro plate (350 μl volume size); 4=liquid sample; 5 are magnetizable rectangular stainless steel bodies (3×1.6×1.9 mm) which by movement of the magnet and application of magnetic force jumps up, rolls and scrapes against the stained fabric while simultaneously depositing liquid sample on the fabric.

Example 3

Testing Carbohydrase

The test device of example 2 was used to test a carbohydrate hydrolyzing enzyme. A knitted cotton fabric coated with tamarind seed flour and carbon black particles was used as stained fabric, which was cut to a dimension fitting a 96 well micro plate.

Preparation 150 ul wash liquor containing 1 mg Ariel Futur liquid detergent and 4 rectangular stainless steel bodies (3×1.6×1.9 mm) was added to each well. Every second array wells also contained 1 ppm of a Xyloglucanase from *Bacillus licheniformis*.

Process

The micro plate was heated to 40° C. in a water bath and after assembling the stained fabric to the top of the filled micro plate, a strong magnet was moved every two seconds over the stained fabric for 30 minutes.

Result

Figure 2:
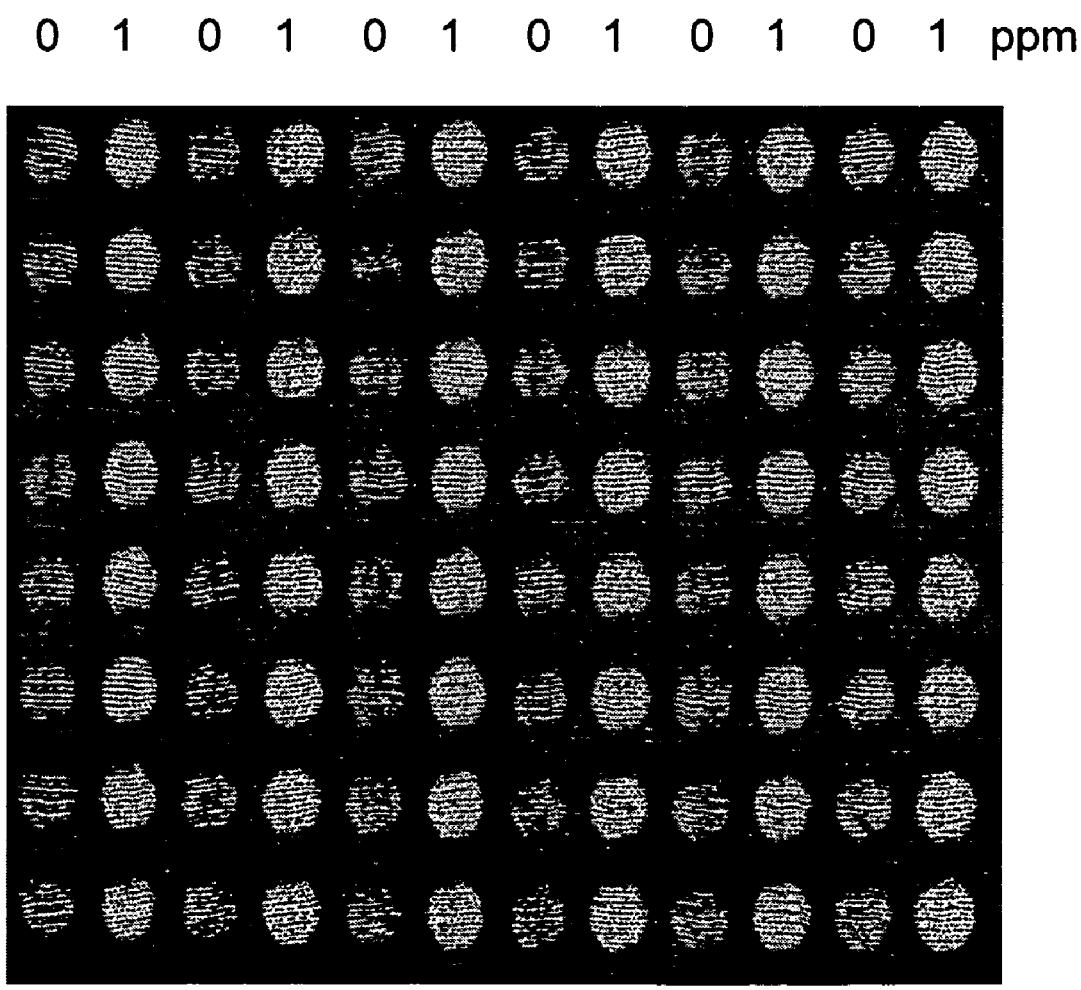
FIG. 2, shows the results of testing effect of a xyloglucanase enzyme on a stained fabric in a test method using a permanent magnet for providing mechanical force to a stained fabric.

Differences in cleaning effect between wells containing the enzyme and wells in which the enzyme is absent was visually detectable as shown in FIG. 2, wherein "0" denotes no enzyme and "1" denotes presence of 1 ppm of enzyme in the test solution. This experiment also shows the benefits of using one coherent stained fabric covering all 96 wells of the micro plate, because although all 96 results are to be measured from this stained fabric, the fabric has a size which is much more easily handled in the measuring procedure, than if 96 individual pieces of stained fabric were to be measured.

Example 4

Correlation of Performance in Test Method Versus Real Wash Procedures

In this example the correlation between real wash performance and using the method of the invention was evaluated for two different enzymes.

Enzyme cleaning effect using the method of the invention was evaluated as described in example 3 using 1 ppm enzymes levels and 8 replica samples per enzyme. The two different enzymes were A: Xyloglucanase from *Bacillus licheniformis* and B: Xyloglucanase from *Bacillus firmus*. The cleaning effect was evaluated by measuring the light reflectance (L-values) of the portions of stained fabric subjected to the test solutions and the mechanical stress. A Spectrafash 500 equipment from "Datacolor International" was used.

Enzyme cleaning effect using a real washing process was evaluated by washing Tamarind seed flour/carbon black stained fabric (5×5 cm swatches) in a Miele W715 washing machine, at 40° C., short cycle together with 0.5 kg realistic items. The same levels and types of liquid detergent and enzyme were used and for each enzyme 8 replica washes were preformed. The cleaning effect was evaluated by measuring L-values of the stained fabric after wash.

Results

The results as given in the table below shows and excellent correlation between using the method and device of the invention and realistic washing processes

| | L-values of treated stains | | | |
|---|---|---|---|---|
| Enzyme | micro plate system | (SD) | washing machine | (SD) |
| A | 62.2 | 0.7 | 65.2 | 1.6 |
| B | 57.0 | 0.5 | 58.9 | 0.7 |
| no enzyme | 54.3 | 0.9 | 50.0 | 1.5 |

Example 5

Container Design 1

A primary assembly suitable for use in testing cleaning ingredients was prepared as shown in FIG. 3(A), wherein (1) are wells of a micro plate having connecting parts between wells which are lowered as compared to the edges of the wells; (2) is a lid having an essentially plane surface facing the micro plate well; (3) the contact zone between the lid and the well, wherein the fabric, when inserted between (1) and (2), is compressed to form a gasket seal. This assembly provides an excellent seal and greatly prevents or inhibits the liquid sample from one well to diffuse or migrate to a neighboring well. This assembly also provides that the stained fabric surface accessible to liquid sample and mechanical stress is at least the same as the area of the opening of the well.

Example 6

Container Design 2

Another primary assembly suitable for use in testing cleaning ingredients was prepared as shown in FIG. 3(B), wherein (1) are wells of a micro plate having connecting parts between wells which are lowered as compared to the edges of the wells; (2) is a lid having elevations fitting into depressions formed around the wells in the micro plate; (3) is the contact zone between the lid and the micro plate well, wherein the fabric, when inserted between (1) and (2), is compressed to form a gasket seal. This assembly provides a slightly poorer sealing effect than the assembly of example 5, but has the advantage that the micro plate part of the contact zone is subjected to less wear upon use and has increased durability. Also the this assembly provides for the stained fabric surface accessible to liquid sample and mechanical stress being at least the same as the inner area of the well opening.

Example 7

Container Design 3

Another primary assembly suitable for use in testing cleaning ingredients was prepared as shown in FIG. 3(C), wherein (1) are wells of a micro plate having connecting parts between wells which are lowered as compared to the edges of the wells; (2) is a lid having elevations fitting into the opening of the well (like a cork) and to depressions formed around the well in the micro plate; (3) is the contact zone between the lid and the micro plate well, wherein the fabric, when inserted between (1) and (2), is compressed to form a gasket seal. This assembly provides a slightly poorer seal than the assembly of example 5, but as in example 6 possesses increased durability because the micro plate part of the contact zone is subjected to less wear upon use.

Example 8

Container Design 4

Another primary assembly suitable for use in testing cleaning ingredients was prepared as shown in FIG. 3(D), wherein (1) are wells of a micro plate having connecting parts between wells which are heightened as compared to the edges of the wells; (2) is a lid having elevations fitting into the opening of the wells (like a cork); (3) is the contact zone between the lid and the micro plate well, wherein the fabric, when inserted between (1) and (2), is compressed to form a gasket seal.

Example 9

Container Design 5

Another primary assembly suitable for use in testing cleaning ingredients was prepared as shown in FIG. 3E, which is similar to the assembly of example 6, with exception that the elevations of the lid forms curves instead of straight tilted lines. This provides an increased durability.

Example 10

Container Design 6

An another primary assembly suitable for use in testing cleaning ingredients was prepared as shown in FIG. 3F, which is similar to the assembly of example 8, with exception that the elevations of the lid forms curves instead of straight tilted lines. This provides an increased durability.

Example 11

Container Design 7

Figure 4:
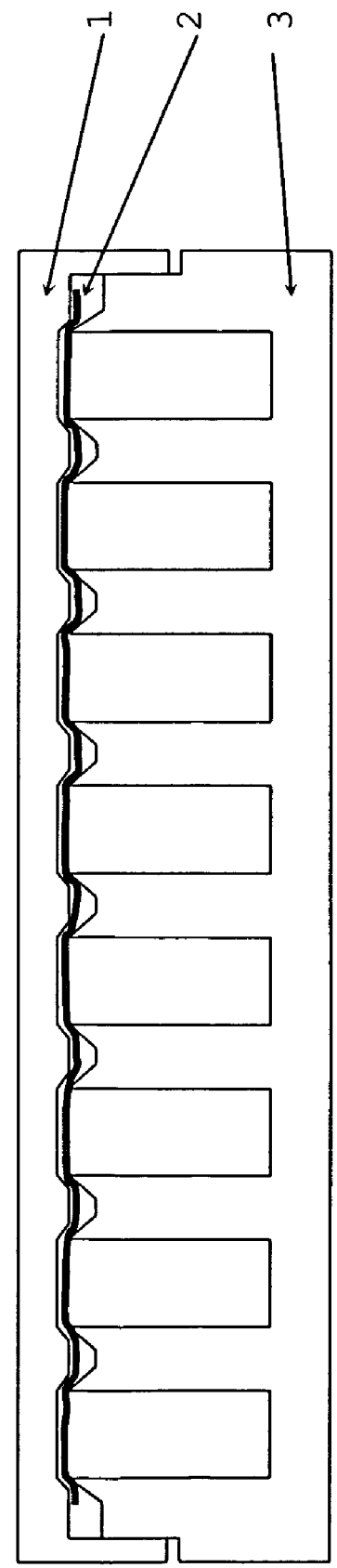
FIG. 4 shows a cross section an assemble comprising a micro plate fitted with a lid and a stained fabric, the assembly being suitable for use in testing effects of cleaning ingredients.

An another primary assembly suitable for use in testing cleaning ingredients was prepared as shown in FIG. 4, which is similar to the assembly of example 6, with the exception that this assembly was made in the standard format of a 96 well plate with standard size of wells and distances between wells. Accordingly, this assembly will fit into standard equipment developed for this format. (1) is the support lid, (2) is the stained fabric and (3) is the micro plate.

Example 12

Testing System 2

Figure 5:
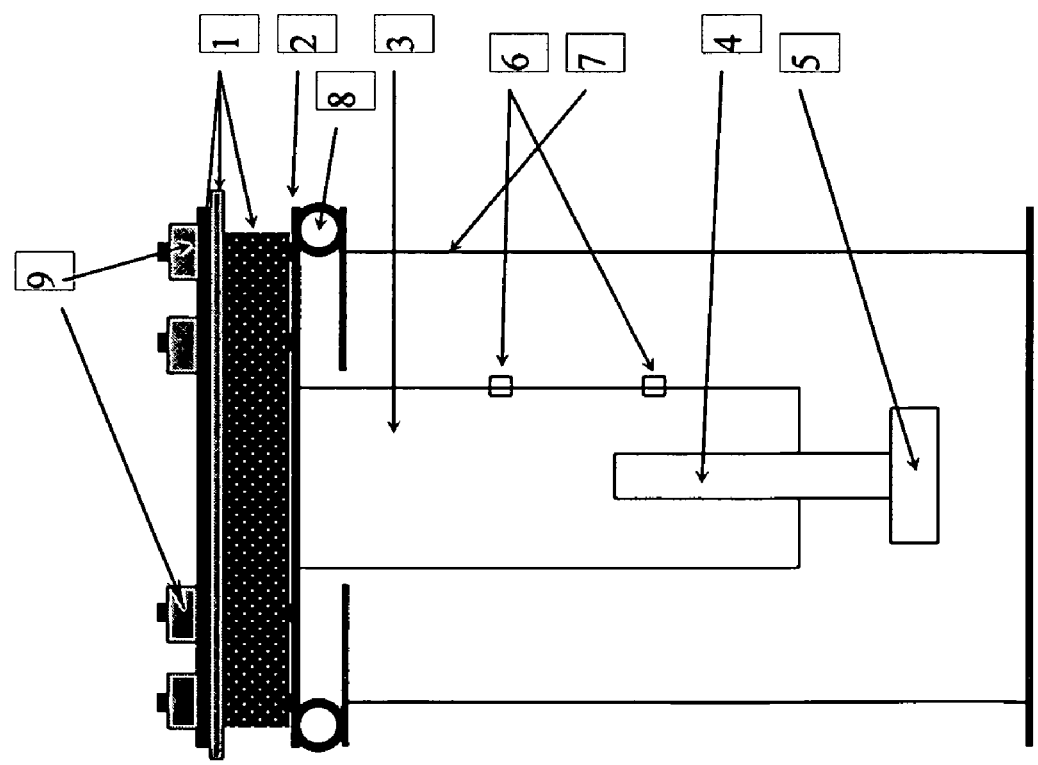
FIG. 5 shows an assembly such as given in FIG. 4, mounted on a device for generating mechanical force.

A secondary assembly which further comprises a device for providing mechanical force to the stained fabric was prepared as shown in FIG. 5. In this secondary assembly a primary assembly of the type described in example 11 was fastened to a NTK 15 or NTK 25 type pneumatic flask vibrator available from Copenhagen Vibrator Products, Industrivej 15, 4652 Hårlev, Denmark. This construction is showed in FIG. 5, wherein the primary assembly (1) is mounted with bolts (9) on the top side of a rigid plate (2) and a cylinder (3) is mounted on the down side of the rigid plate (2), The cylinder (3) surround a piston (4) with mass elements (5), capable of moving in the longitudinal direction of the cylinder (3) by applying compressed air to valves or apertures (6) in the cylinder. This rigid plate (2) is rested on a stationary support (7) via rubber connectors (8) which is capable of moderating the vibrating force.

Example 13

Effect of Mechanical Stress

Five different microbially derived xyloglucanases; A, B, C, D, E and one cellulase F were tested with (+) and without (−) using steel beads to provide mechanical stress using the test plate of example 11 fitted in the assembly of example 12. Each enzyme were diluted to give a final concentration of $1/16$, $1/8$, $1/4$, $1/2$, 1, and 2 ppm in the 96 well plate containing 6.7 g/l Ariel Color liquid detergent in 15° dH $H_2O$ in a final volume of 160 µl. Eight repeats of each dilutions were carried out. A fabric stained with tamarind gum and carbon black was used. Each well in which high mechanical stress were to be tested contained 3×2 mm steel beads, wells wherein low mechanical stress where to be tested contained no steel beads. Using this construct the stained fabric was which was washed for 30 min at 26° C. under vibration by the vibrating device. The cleaning results were evaluated by measuring light reflectance of the cleaned fabric.

Results

| Enzyme dose | Enzyme | | | | | | | | | | | |
|---|---|---|---|---|---|---|---|---|---|---|---|---|
| μg/ml | A− | A+ | B− | B+ | C− | C+ | D− | D+ | E− | E+ | F− | F+ |
| 0 | 1718 | 1882 | 1694 | 1880 | 1884 | 1919 | 1654 | 2012 | 1552 | 2105 | 1648 | 1929 |
| 0.0313 | 1671 | 2003 | 1679 | 2025 | 1670 | 2015 | 1925 | 1830 | 1836 | 2116 | 1793 | 1940 |
| 0.0625 | 1745 | 1992 | 1859 | 2215 | 1620 | 2046 | 1650 | 1970 | 1746 | 1977 | 1706 | 1924 |
| 0.125 | 1808 | 2168 | 1914 | 2105 | 1605 | 1903 | 1746 | 2056 | 1686 | 1989 | 1698 | 1946 |
| 0.25 | 1741 | 2343 | 1693 | 2321 | 1814 | 1978 | 1805 | 2106 | 1775 | 2256 | 1687 | 1997 |
| 0.5 | 1862 | 2524 | 1867 | 2381 | 1799 | 2224 | 1794 | 2186 | 1607 | 2312 | 1714 | 1848 |
| 1 | 1884 | 2639 | 1804 | 2468 | 1784 | 2086 | 1808 | 2127 | 1830 | 2156 | 1747 | 1836 |
| 2 | 1815 | 2424 | 1743 | 2320 | 1768 | 2190 | 1712 | 2234 | 1693 | 2298 | 1685 | 1833 |

The results shows that for each enzyme treatment with the steel beads increases removal of stain, similar to results obtainable for real washing processes. Also a ranking of the different enzyme efficiency could be was deducted from the results, rendering enzyme A the most efficient enzyme.

Example 14

Test of Non-Cellulolytic Enzymes with no Body to Induce Mechanical Stress

In order to show the applicability of the system to other enzymes a series of proteases were tested using the assembly of example 12 using both commercial 96 well test plate and the custom made test plate of example 11. The proteases were mixed in amounts of 0, 5, 10, 20 and 40 nanomoles per liter to samples of a commercial OMO color detergent dissolved in 15° dH water yielding a pH of about 10.4 in the solution. The test samples were transferred to the wells of the test plates, and all well openings in each test plate were subsequently covered by one single coherent EMPA 117 stained test fabric and a lid. The wells of the test plate did not contain a body for providing mechanical force.

Figure 6:
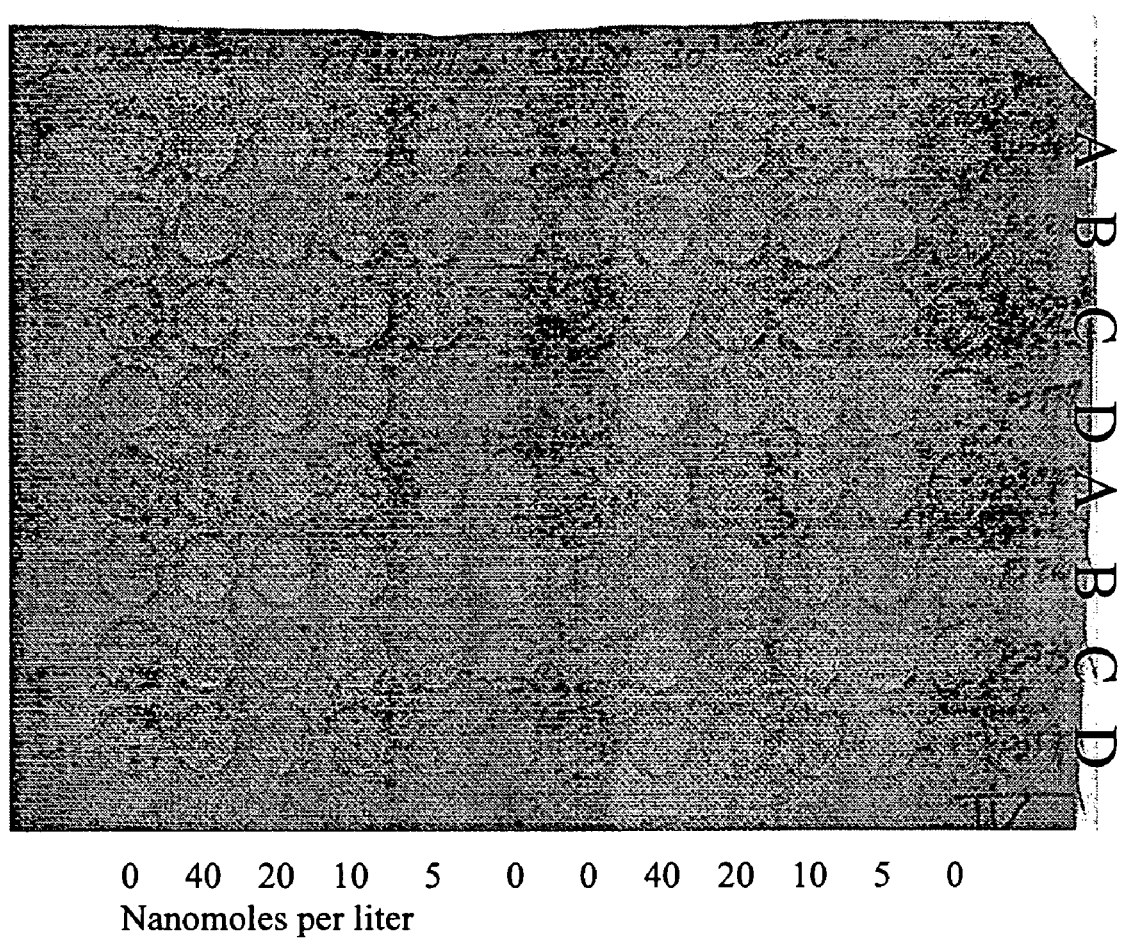
FIG. 6 shows the results of testing different protease enzymes in a commercial 96 well test plate with a single coherent stained fabric covering all well openings of the commercial plate, the test plate and stained fabric mounted on the device of FIG. 5 without addition of a movable body to the wells.
Figure 7:
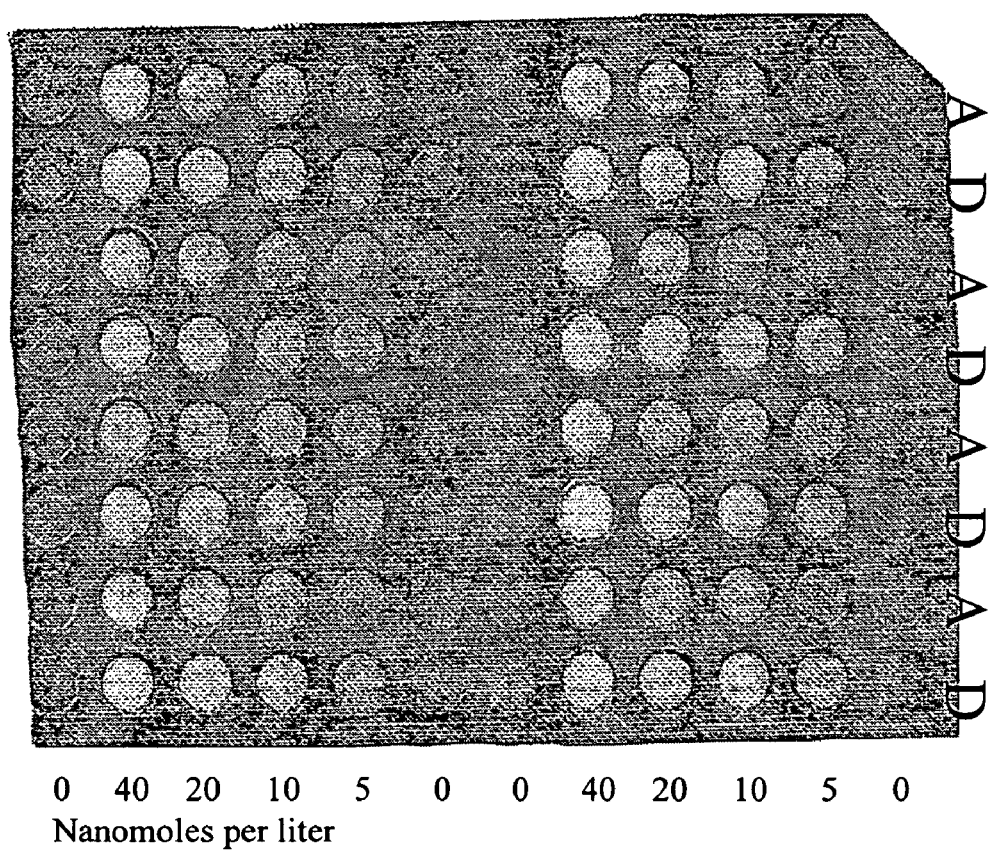
FIG. 7 shows the results of testing different protease enzymes in the a 96 well custom made test plate assembly according to FIG. 4 with a single coherent stained fabric covering all well openings of the plate, the test plate and stained fabric mounted on the device of FIG. 5 without addition of a movable body to the wells.

The test plates were then mounted on the assembly of example 12 and vibrated at 30° C., and after this treatment each part of the test fabric corresponding to single samples was evaluated. For both plates a clear indication of samples having a high protease concentration was observed, so that samples having higher protease concentrations had removed more stain from the fabric in an area corresponding to the circumferences of the wells. However, for the commercial plate it was evident that the test samples had spread beyond the area of the stained fabric which was circumferenced by the edge of the well (i.e. the area of the opening of the well) so that stain removal was also seen outside the areas of the stained fabric directly exposed to the test samples. Accordingly, the test samples were leaking from the wells or migrated through capillary effects to areas of the stained test fabric not directly covering the opening of the wells. This phenomenon obscured the results of the test. The results of using a stained fabric with a commercial 96 well test plate can be seen in FIG. 6. In FIG. 6 A-D represents different proteases tested at different concentrations.

Using the custom made test plate, the test samples were effectively confined to act only on the area of the stained fabric covering the opening of the well. Consequently very clear cleaning results were obtained, where the effect of different concentrations could easily be identified. Moreover it was possible to visually determine that protease D had better cleaning performance than protease A. This result also show that for proteases and other non-cellulose hydrolyzing enzymes application of mechanical force by means of a solid body colliding with the stained fabric is not necessary for these enzymes. Moreover, this method and system generated results which are comparable to the performance of the test enzyme under real washing conditions those obtainable with a real washing procedure.

Example 15

Screening for Pectate Lyases with Improved Stain Release Properties 23 different pectate lysases were tested for their ability to remove pectate stain from fabric using a test devise which was a carousel construction comprising (a) a horizontal rotatable support disc comprising means for fastening, in a position different from the rotational centre, of 4 96-well microplates sealed with stained fabric. Each well contained in addition to liquid sample 5 solid magnetic implements for providing mechanical stress.

(b) a fixed permanent magnet which was positioned to enable passing the microplates under the magnet by rotating the support disc in sufficient proximity to cause the magnetic implements in the wells to be attracted by the magnet and to collide with the stained fabric.

(c) an electric engine for rotating the support disk at a constant rate

Samples of pectate lyases (8 replicas) at two different concentrations (1 ppm and 0.1 ppm) were mixed, in each well, with 150 μl of a commercial detergent dissolved in city water (2.5 mmol/l hardness). Knitted cotton fabrics impregnated with a citrus peel based pectate stain was positioned over the microplates covering all the wells and the fabric was fixed using a lid. A washing process was now simulated by rotating the support disk at a constant speed so that the microplates continuously passed closely under the magnet, whereby the magnetic implements were lifted towards the magnet thereby colliding with the fabric sealing the wells. This process was continued for 30 minutes at 40° C.

Figure 8:
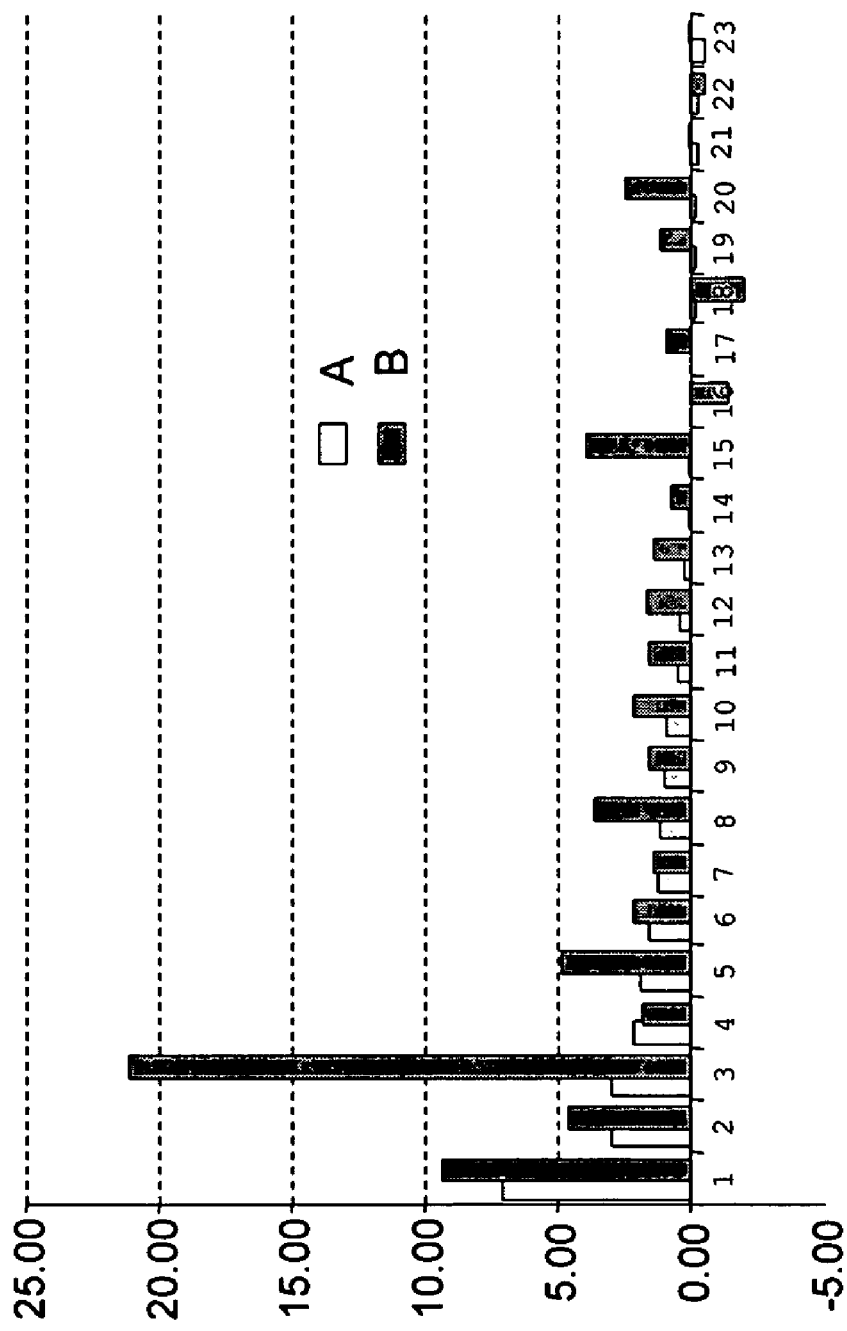
FIG. 8 shows the cleaning performance of 23 different pectate lyases and concentration 0.1 ppm (A) and 1 ppm (B) when tested using the method and system of the invention in terms of light reflected from stained fabrics cleaned with the pectate lyases.

After completing the simulated washing process the light reflectance of stained fabrics were measured as an indication of how much of the stain which had been cleaned off by each pectate lyase. The results were inserted in a plot (FIG. 8), where the pectate lyases were plotted at the X-axis (numbers 1-23) and the relative reflectance was plotted at the Y-axis. In the plot higher relative reflectance means higher cleaning performance of the pectate lyase. In the plot series A indicates high pectate lyase concentration in washing liquor (1 ppm) and series B indicates low concentration of pectate lyase (0.1 ppm).

The results clearly shows that some pectate lyases are significantly better than others in removing citrus peel stains. Pectate lyase 1 is clearly best at low dose while pectate lyase 3 is clearly best at high dose. The results also shows, in conjunction with examples on the present invention yielding results very close to those obtained in real washing processes, screening procedures, involving huge amounts of samples, can be made using the method of the present invention, which would be extremely demanding, if not impossible, should the screening have been made using real washing procedures.

Example 16

Screening for Effects of Water Hardness in Different Washing Conditions

This example shows that the methods and systems of the present invention also is very useful for testing and screening of compounds present in a washing liquor, which do not possess cleaning properties in themselves, but which interferes in the washing process by affecting the action of active cleaning compounds and that the methods and systems of the present invention generates result fully comparable with those obtained in a commercial washing machine.

In this example it was tested how two different levels of water hardness (0 mM and 8 mM) affected the washing process at European washing condition in the method of the invention, at North American washing conditions in the method of the invention and at European conditions in a commercial washing machine.

For the European conditions washing liquors containing 4 g/l of a commercial European liquid detergent was prepared with water of low and high hardness.

For the North American conditions a washing liquor containing 1.2 g/l of a commercial North American liquid detergent was prepared with water of low and high hardness.

8 different stains were prepared on knitted cotton fabrics.

For European conditions the stained fabrics were tested both by the method of the invention as in example 15 (96 well microplates in the carousel system) and in a commercial European washing machine (Miele) at 40° C. and a 30 minutes wash time. For the North American conditions the stained fabrics were tested by the method of the invention as in example 15 at 32° C. and a 12 minutes wash time. 12 replicas were made of each sample to estimate experimental errors.

The cleaning effect of each sample was evaluated by measuring the light reflectance of the stained fabric after cleaning.

The results showed that under European conditions the method of the present invention generates the same or very similar stain removal profiles as obtained in a full-scale European wash machine.

The results also showed that use of the present invention enables quantitative prediction of differences in cleaning performance between European conditions and North American conditions. The results showed substantial differences for some stains between North American versus European conditions. Overall, the system proved to be fully functional also for screening other compounds than those directly involved in the cleaning process such as salts, builders, polymers and the like levels.

Example 17

Screening Cleaning Compositions for Hard Surface Cleaning

This example shows that the methods and systems of the present invention also is very useful for testing and screening of improved compounds or compositions used for cleaning hard surfaces and that the method and system of the present invention generates result fully comparable with those obtained in internationally recognized test methods.

In this example the cleaning effect of 3 different commercially available cleaning compositions agents and one new composition were tested in the methods of the present invention and the recognized "wet-abrasion-scrub-test" conventionally used for testing such compositions.

In the Wet-Abrasion-Scrub Tester four separate sponges with cleaning composition are scrubbing in a controlled manner over four soiled hard surfaces. The stain contains a mixture of grease and particular dirt, which have been heat treated to get a hard, tenacious soil on the hard surface. The sponges with the cleaning composition are moving periodically over the soiled hard surfaces until the tiles are clean and the numbers of strokes are counted. These numbers are used to calculate the Cleaning Index, which is always referring to a benchmark or reference product. However this approach is a very tedious, labor and time intensive procedure.

For the Wet-Abrasion-Scrub test stainless steel metal plates were soiled with an oil mix and Carbon Black based soiling. The cleaning test was executed with four plates at room temperature (20° C.) in 2 minutes. The strokes were counted and calculated with "Mr. Proper All Purpose Cleaner" as the reference.

For the test according to the present invention stainless steel metal plates were cut to the size of a 96 well micro-plate and soiled with an oil mix and Carbon Black based soiling. All 96 wells were filled with 150 ml of the cleaning compositions (14 replicates). A test was conducted as in example 15 at room temperature (20° C.) in 2 minutes.

Assessment of the cleaning result was achieved by measuring light reflectance (via image scan and calibrated against L scale, wherein the pixel density gave information about stain removal).

Figure 9:
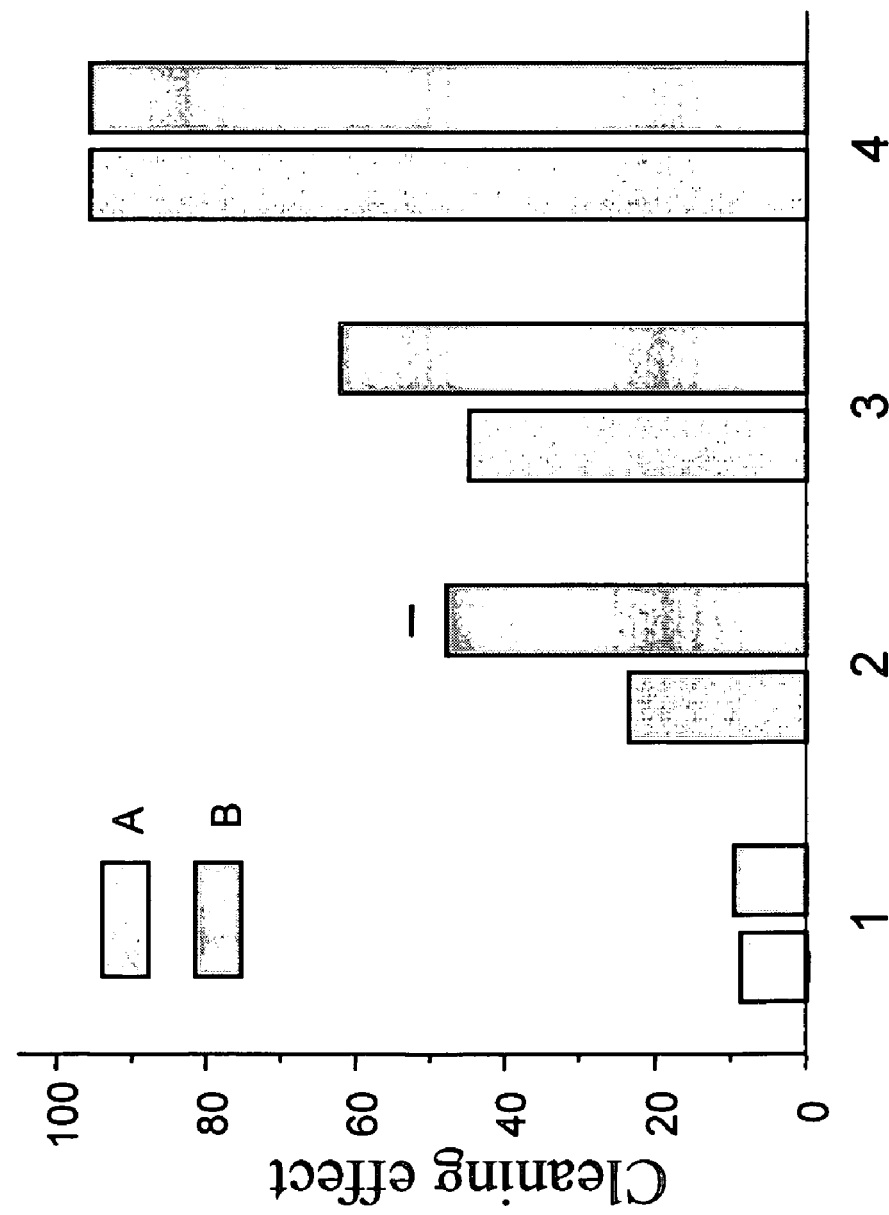
FIG. 9 shows the cleaning performance of 4 different hard surface cleaning products (3 commercial and 1 experimental) measured using conventional techniques (B) and the using the method and system of the present invention (A).

The results were inserted in a plot (FIG. 9), where the cleaning compositions were plotted at the X-axis (1=AJAX all purpose cleaner, 2=Mr. Proper all purpose cleaner, 3=new cleaning composition and 4=Mr. Proper W3-spray with bleach) and the cleaning effect was plotted at the Y-axis. In the plot series A indicates results from the method of the invention and B indicates results obtained with the wet-abrasion-scrub-test.

The results clearly shows both systems that some cleaning compositions are more efficient than others in removing the selected soiling. The results also shows that results of the method and system of the present invention are fully comparable to those of the far more tedious, laborious and time intensive wet-abrasion-scrub procedure and that the method of the present invention may advantageously replace the conventional method.

Example 18

Testing Effect of Water Hardness on Cleaning Performance of Protease Enzymes

Following example 16 the method of the present invention was used to evaluate the effect of water hardness in the washing liquor on the removal of different grass stains impregnated on fabric.

5 in-house stained fabric, impregnated with 5 different grass stains and 2 commercially available grass stained fabric (EMPA Switzerland) were tested.

Two washing liquors were prepared by dissolving 4 g/l of a commercial detergent in either soft water (0 mM $Ca^{2+}/Mg^{2+}$) or hard water (10 mM $Ca^{2+}/Mg^{2+}$).

96 well microplates were filled with 150 ml wash solution prepared from either hard or soft water in 8 replicates grass stained fabrics were fitted to the microplates. The stained fabrics were treated with the wash solutions for 30 minutes at 40° C. as in example 15 using the carousel system. Assessment of the stain removal was done by measing the light reflectance of the cleaned fabric by image scanning calibrated against L scale.

Figure 11:
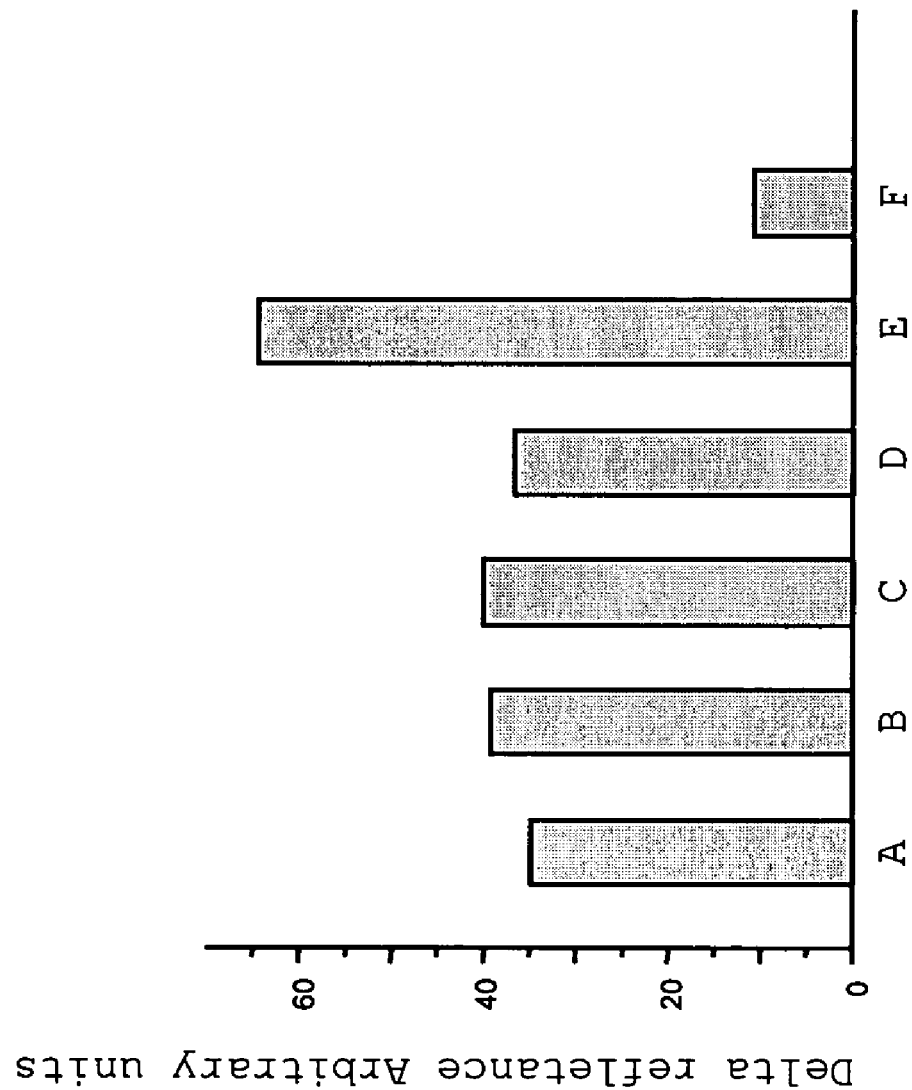
FIG. 11 shows the difference in cleaning performance of a commercial detergent when dissolved in soft water (0 mM $Ca^{2+}/Mg^{2+}$) and in hard water (10 mM $Ca^{2+}/Mg^{2+}$) against different grass (A-F) impregnated on fabric when tested using the method and system of the invention.

The results were inserted in a plot (FIG. 11), wherein the fabric having different grass stains were plotted on the X-axis (A=in house made grass stain 1, B=in house made grass stain 2,=in house made grass stain 3, D=in house made grass stain 4, E=in house made grass stain 5, F=commercial grass stain EMPA 164). The reflectance of cleaned fabric (0 mM hardness) minus reflectance of cleaned fabric (10 mM hardness) were plotted on the Y-axis. The results indicates that the water hardness have a tremendous effect on the cleaning performance of the detergent on grass stains, while it is different from different stain types. In FIG. 10 higher values means more lowering of the performance at high water hardness. Such results easily obtainable by the method and system of the invention is important when developing improved detergent compositions.

Below graph shows the difference in SRI values between 0 and 10 mM water hardness. It seems the stain removal inhibition starts at a range of 1.5 to 2.5 mM, probably due to the insufficient masking of free divalent ions above this range. Pictures of some stains are shown in Appendix 2.

The invention claimed is:

1. A method for testing the cleaning effect of a compound or compositions containing said compound, said method comprising:
   (a) providing an array of containers wherein each said container comprises a liquid sample of less than 10 ml of said compound and a stained surface, wherein the surface is an inorganic surface selected from metal, glass, ceramic, enamel, concrete, rock, marble, gypsum and composite combinations thereof or an organic surface selected from wood, paper, leather, fur, paint and fabric,
   (b) applying mechanical stress to said stained surface by contacting said stained surface with a body present in said liquid sample, wherein the body comprises a ferromagnetic metal,
   (c) evaluating the cleaning effect of applying the liquid sample and mechanical stress on said stained surface.

2. The method of claim 1, wherein the compound is selected from the group consisting of enzymes, enzyme stabilizers, enzyme inhibitors, enzyme enhancers, enzyme cofactors, builders, builder systems, bleach systems, bleach activators, metal-containing bleach catalyst, optical brighteners, nonionic-, anionic-, cationic-, zwitterionic and amphoteric surfactants, fabric softening agents, softening clays, clay flocculants, dye-transfer inhibiting agents, polymeric soil release agents, clay soil removal agents, anti-soil redeposition agents, polymeric dispersing systems, chelating agents, alkoxylated polycarboxylates, perfumes, perfume systems, carrier systems, dyes and pigments, fabric care agents and color care agents.

3. The method of claim 2, wherein the enzymes are alkaline.

4. The method of claim 1, wherein the liquid sample has a volume selected from 5-95% of the volume of the container.

5. The method of claim 1, wherein the surface is a fabric.

6. The method of claim 1, wherein the array of containers is a micro plate.

7. The method of claim 1, wherein the array of containers is a micro plate comprising 24, 96, 384 or 1536 containers or wells.

8. The method of claim 4, wherein the volume of the container is selected from the group consisting of 3.7 mL, 320 μL, 160 μL and 14 μL.

9. The method of claim 5, wherein the fabric is made from natural plant fibers, animal based fibers, synthetic fibers, or a combination thereof.

10. The method of claim 5, wherein the fabric is woven, non-woven, soft or stiff.

11. The method of claim 5, wherein the fabric is a cellulose containing fabric.

12. The method of claim 1, wherein the stained surface comprises a traceable compound or composition associated with the surface.

13. The method of claim 12, wherein the traceable compound is selected from the group consisting of a light absorbing dye, a fluorescent dye, a radioactive compound, a reactive compound, and a catalyst or activator capable of performing measurable interaction with a substrate.

14. The method of claim 12, wherein the traceable compound is comprised in a particulate composition.

15. The method of claim 12, wherein the traceable compound is comprised in carbon particles or iron oxide particles.

16. The method of claim 12, wherein the traceable compound is comprised in a soiling composition.

17. The method of claim 16, wherein the soiling composition is a naturally occurring soiling selected from grass, mud, clay, coffee, tea, blood, egg, lard and mold.

18. The method of claim 16, wherein the soiling composition is a processed naturally occurring soiling selected from butter, processed meat, dyed lard, oil, make up, spice blends, processed tomatoes, chocolate, ice cream, cacao, baby food, a refined protein composition, a refined polysaccharide composition, a refined fatty acid composition and a refined triglyceride composition.

19. The method of claim 1, wherein the body comprises iron or an alloy thereof.

20. The method of claim 1, wherein the body has a surface comprising at least one edge or corner.

* * * * *